United States Patent [19]

Urso

[11] Patent Number: 4,691,688
[45] Date of Patent: Sep. 8, 1987

[54] SAFETY HEATER

[76] Inventor: Charles L. Urso, 215 Newton St., Waltham, Mass. 02154

[21] Appl. No.: 919,086

[22] Filed: Oct. 14, 1986

Related U.S. Application Data

[63] Continuation-in-part of Ser. No. 717,310, Mar. 29, 1985, abandoned, which is a continuation-in-part of Ser. No. 644,987, Aug. 28, 1984, abandoned, and Ser. No. 642,059, Aug. 20, 1984, abandoned.

[51] Int. Cl.$^4$ ............................................. A61F 7/08
[52] U.S. Cl. .................................. 126/208; 126/204; 126/93; 126/59; 126/59.5
[58] Field of Search ............... 126/266, 265, 262, 208, 126/204, 93, 95, 84, 85 R, 58, 59, 59.5; 431/200, 201, 344, 343, 354

[56] References Cited

U.S. PATENT DOCUMENTS

| | | |
|---|---|---|
| 877,349 | 1/1908 | Little . |
| 1,023,055 | 4/1912 | Wilson . |
| 2,567,323 | 9/1951 | Cyphert . |
| 2,843,105 | 7/1958 | Badish . |
| 2,845,924 | 8/1958 | Benda . |
| 2,904,031 | 9/1959 | Scott . |
| 4,351,314 | 9/1982 | Morton . |
| 4,475,532 | 10/1984 | Woods ................................ 126/204 |

Primary Examiner—Randall L. Green
Attorney, Agent, or Firm—Hamilton, Brook, Smith & Reynolds

[57] ABSTRACT

A portable heater comprising a double-wall vessel which forms a combustion chamber and encloses a suitable fuel. Air passages provide an airflow through the vessel for supporting combustion. Also included are endless conduits which entrap displaced fuel to prevent it from escaping from the heater through the air passages. Thus, fuel is prevented from escaping from the heater in all positions of the same in the event that the heater is dropped or otherwise upset. A set of cooling fins, encircling a fuel holder, cool the fuel to help maintain an even burn rate. The heater further includes an adjustable flame attenuator for selective heat control. At a low heat setting the invention may be used as a personal or close contact heater wherein an outer wall serves as a guard for preventing contact burns.

23 Claims, 10 Drawing Figures

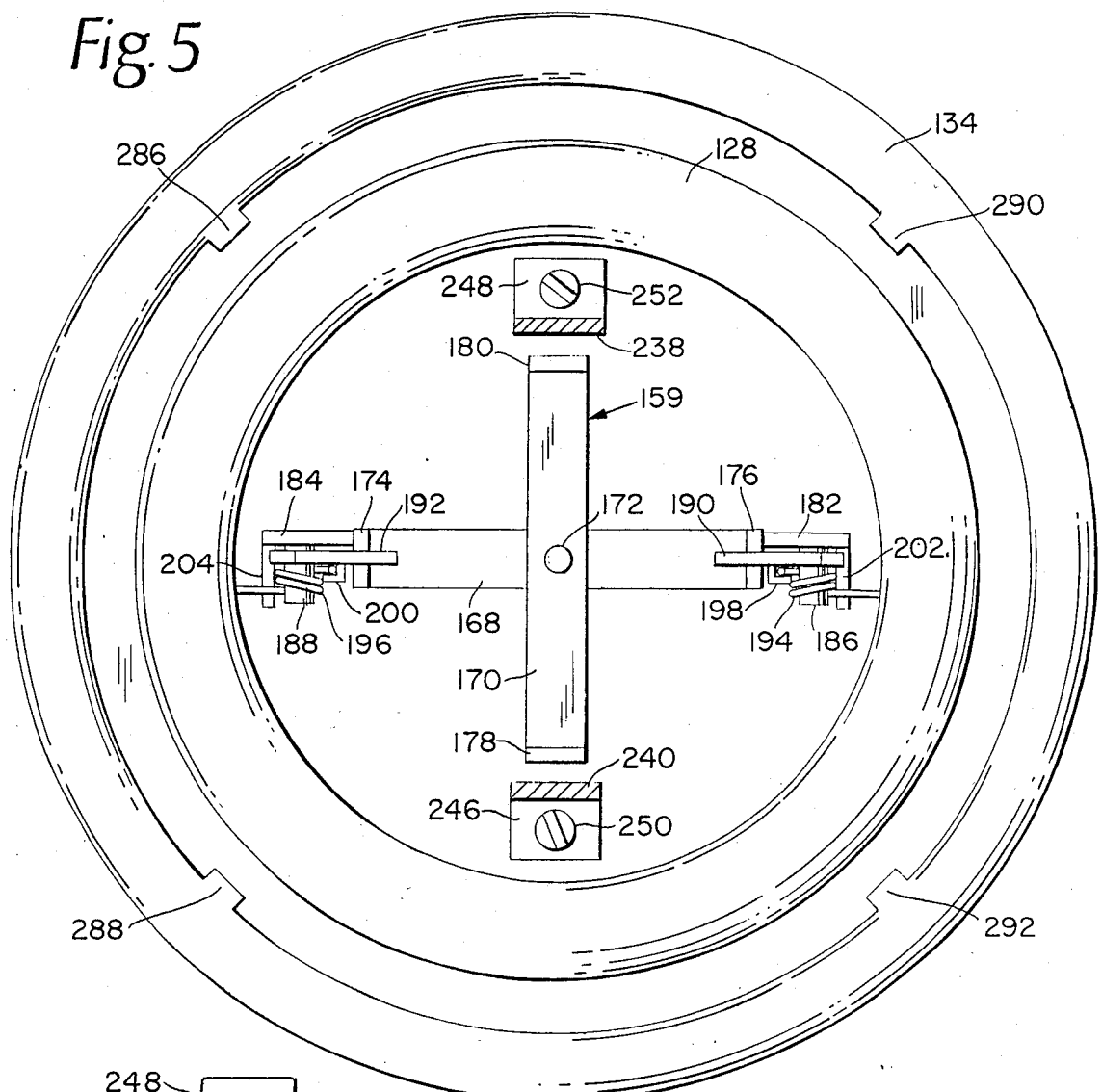
Fig. 5
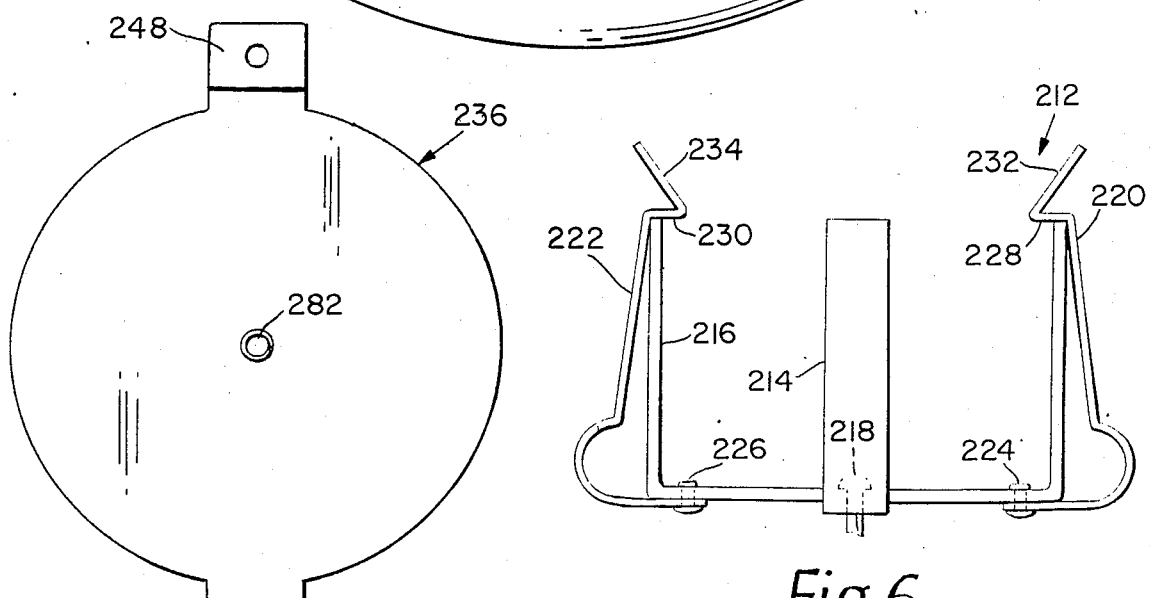
Fig. 7
Fig. 6

SAFETY HEATER

RELATED APPLICATIONS

This is a continuation-in-part of application Ser. No. 717,310 filed Mar. 29, 1985 (now abandoned) which is a continuation-in-part of Ser. No. 644,987 filed Aug. 28, 1984 (now abandoned) and of Ser. No. 642,059 filed Aug. 20, 1984 (now abandoned).

TECHNICAL FIELD

This invention relates to portable heaters and specifically to portable heaters which utilize combustible fuels.

BACKGROUND OF THE INVENTION

Portable heaters utilizing combustible materials as fuel have long been known in the art. Need for these devices often arises in locations where household electric power is unavailable. Typical locations where such devices are needed, therefore, include ice fishing sites, campsites, remote cabins, and spectator sports events. Widespread use of such portable heaters, however, has been restricted by potential hazards which stem from the use of combustible materials. Problems which have been encountered include fires, chemical burns, and thermal burns. Many of these accidents have occurred as result of dropping or knocking the heaters over wherein there is spillage or escape of fuel. Further, such devices are generally unsuitable for use in the presents of children unless they are constantly monitored. The necessity of constantly monitoring such devices further restricts their use.

It is an object of this invention, therefore, to provide an improved portable heater which includes safety features for the prevention of accidental fire or burns.

SUMMARY OF THE INVENTION

The present invention comprises a double-wall vessel which forms a combustion chamber and encloses a suitable fuel. Air passages provide an airflow through the vessel for supporting combustion. Also included are endless conduits which entrap displaced fuel to prevent it from escaping from the heater through the air passages. Thus, fuel is prevented from escaping from the heater in all positions of the same in the event that the heater is dropped or otherwise upset.

One of the embodiments of the heater includes a set of cooling fins, encircling a fuel holder, to cool the fuel to help maintain an even burn rate. The heater further includes an adjustable flame attenuator for selective heat control. At a low heat setting the invention may be used as a personal or close contact heater wherein an outer wall serves as a guard for preventing contact burns.

BRIEF DESCRIPTION OF THE DRAWINGS

The accompanying drawings, in combination with the description herein, illustrate features and advantages of the invention. Like reference characters in different views refer to the same parts. The drawings are intended to illustrate principles of the invention and are not necessarily to scale and in which drawings:

FIG. 5 is a top plan view of the invention of FIG. 4 with an upper subassembly removed;

FIG. 6 is a side elevation of an alternate embodiment of a fuel can holder;

FIG. 7 is a plan view of a baffle plate and baffle plate supports of the invention of FIG. 4;

DETAILED DESCRIPTION OF THE INVENTION

First Embodiment

Figure 1:
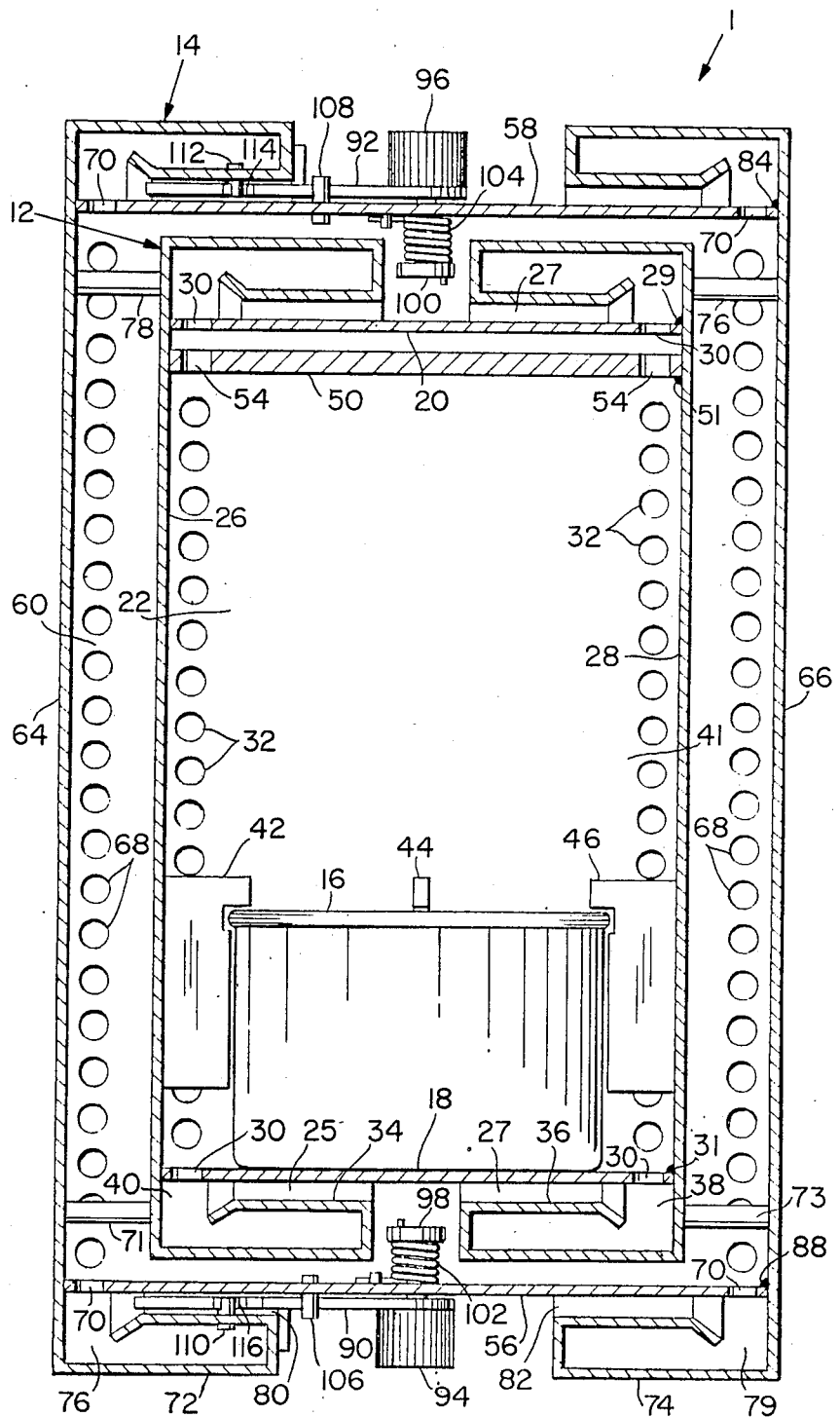
FIG. 1 is a cross-sectional view of the invention taken along the line 1—1 of FIG. 2.

A portable safety heater 1 embodying the principles of this invention is shown in cross-section in FIG. 1. The safety heater 1 comprises a rectangular double-walled vessel having an inner enclosure 12 coaxially positioned in an outer enclosure 14. A fuel can 16 is seated inside the inner enclosure 12 and is used to heat the heater and its surrounding environment.

The inner enclosure 12 forms a six-sided rectangular box which includes two inner short sides 18, 20, two inner long sides 22, 24 (FIG. 2), and two inner caps 26, 28.

Figure 2:
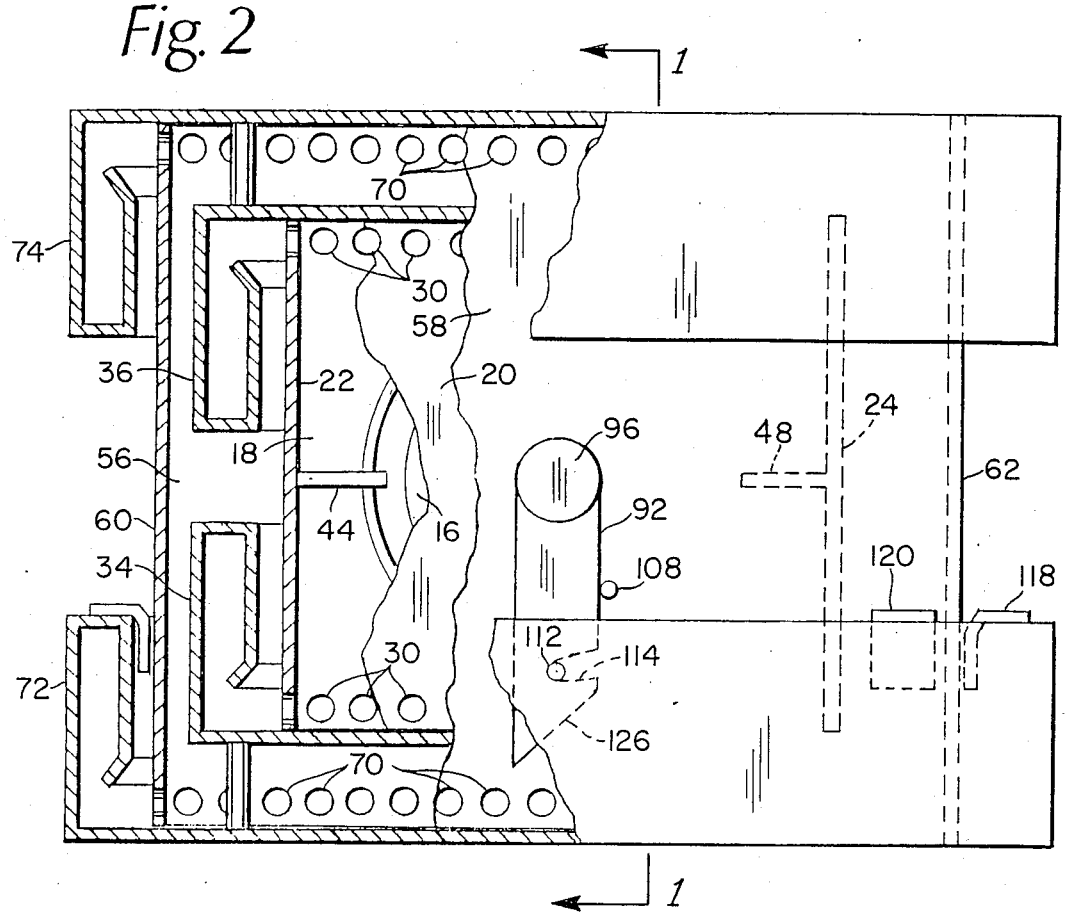
FIG. 2 is a partially broken-away top view of the invention FIG. 1.

The short sides 18, 20 are pierced through two of their peripheral edge portions by air holes 30 (best seen in FIG. 2). Similarly, long sides 22, 24 are pierced through their long peripheral edge portions by air holes 32 which are a continuation of air holes 30. These air holes 30, 32 allow air circulation, or draft, to pass into and out of the inner enclosure when the fuel in fuel can 16 is ignited.

The inner caps 26,28 each include peripheral portions shaped to form four-sided continuous conduits 34, 36 which surround the inner short and long sides. Entrance portions 38, 40 of respective conduits 36, 34 are adjacent to and in a spaced relationship with short sides 18, 20 and long sides 22, 24 of the inner enclosure 12 and correspond with the air holes 30, 32. As a result, loosened fuel or debris from fuel can 16 is caught in the conduits rather than passed out of the heater 1 when the same is turned or upset. Air passages 25, 27, surrounding the inner long and short sides, are provided to permit gaseous passage past the conduits.

Cap 28 is fixedly attached to short sides 18, 20 and long sides 22, 24 by welds 29, 31. Cap 26, however, is removable for maintenance of the heater as explained hereinafter.

Contained within the inner enclosure 12 is the fuel can 16 and a combustion chamber 41. The fuel can 16 is held in place by brackets 42, 44, 46, 48 (FIGS. 1 and 2). The brackets are equally spaced and each is welded to a respective side of the inner enclosure. The can 16 is seated on the inner face of short side 18.

The fuel can preferably contains a jelled or semi-solid fuel, but other fuel types, including solid fuel, may be substituted.

A baffle plate 50 (FIG. 1) having dimensions substantially the same as short side 20 is positioned, within inner enclosure 12, opposite the open end of fuel can 16. The baffle plate 50 is held in position by weld 51 attaching it to cap 28. The plate 50 also has air holes 54 which correspond with air holes 30, 32 in the inner enclosure and thereby permit gaseous passage.

The outer enclosure 14 surrounds inner enclosure 12 on all sides. The outer enclosure is larger but otherwise similar in construction and orientation to enclosure 12. Outer enclosure 12 forms a six-sided rectangular box having two outer short sides 56, 58, two outer long sides 60, 62 (FIG. 2), and two outer caps 64, 66.

The long sides 60, 62 are pierced along their long peripheral edge portions to form air holes 68. Similarly, the short sides 56, 58 are pierced along two of their peripheral edge portions to form air holes 70 (best seen in FIG. 2) which are a continuation of air holes 68 of long sides 60, 62. These air holes, in combination with the air holes 30, 32 in the inner enclosure 12, permit gaseous passage to and from the fuel can 16. Thus, combustion is supported and warmed air is expelled to heat the environment surrounding the heater 1.

The outer caps 64, 66 are held in spaced relation to the inner enclosure 12 by spacer brackets 71, 73, 76, 78. The brackets are permanently affixed at their inner ends to an inner cap and at their outer ends to an outer cap.

The outer caps 64, 66 each include peripheral portions comprising continuous conduits 72, 74 which surround the outer short and long sides. Entrance portions 76, 79, of respective conduits 72, 74, are adjacent to air holes 70 in short sides 56, 58 and air holes 68 in long sides 60, 62 of the outer enclosure 14. These conduits act as redundant safety devices which catch displaced fuel or debris in the unlikely extreme condition that it bypasses the inner conduits 34, 36. Air passages 80, 82, between the outer conduits and the outer long and short sides, provide a means for airflow between the interior of the heater and its outside environment.

Outer cap 66 is permanently affixed to the inner enclosure by spacers 73, 76 and to long sides 60, 62 and short sides 56, 58 by weld joints 84, 88. Outer cap 64, however, is fixed only to removable inner cap 26 by the spacer brackets 71, 78.

Thus constructed the safety heater 1 comprises two detachable subassemblies; a box portion and a cover portion. The box portion includes caps 28, 66 as well as the inner and outer long and short sides. The cover portion includes caps 26, 64, spacers 71, 78, and bracket 42. The cover portion is removable from the box portion of the heater for fuel replacement and maintenance. Alternatively, a closable port can be provided in a side of the heater to allow lighting of the fuel without removal of the cover.

The cover portion is removably secured to the box portion by means of spring latches 90, 92. Each latch 90, 92 is fixed to a respective knob 94, 96 and is pivotally supported by a shaft (not shown) which extends from a knob 94, 96 through an aperture in a short side 56, 58 to a respective spring retainer 98, 100. Each retainer 98, 100 is fixed to its corresponding shaft. Encircling each shaft is a respective torsion spring 102, 104. Each torsion spring is fixed at one end to a spring retainer and at the other end to one of the short sides 56, 58. Each spring 102, 104 is thereby arranged so that its restoring force urges its adjacent latch (90, 92) to a closed, or locked, position against a respective stop 106, 108 (see FIGS. 1 and 2). The stops are permanently affixed to respective short sides 56, 58 of the box subassembly. Cover holding pins 110, 112 are fixed to the cover subassembly at the conduit portion 72 of the outer cap 64. These holding pins 110, 112 are received by respective retaining slots 114, 116 in the latches 90, 92 when the cover is secured to the box.

The cover is removed from the box subassembly when both knobs are turned against spring tension to move latches 90, 92 clear of holding pins 110, 112. Both knobs 94, 96 must be turned simultaneously in order to release the cover; a safety feature that prevents accidental opening of the heater. Since the latching mechanisms are protected by the outer conduits, prevention of accidental opening is further assured. Thus, fires and injury are prevented.

Figure 3:
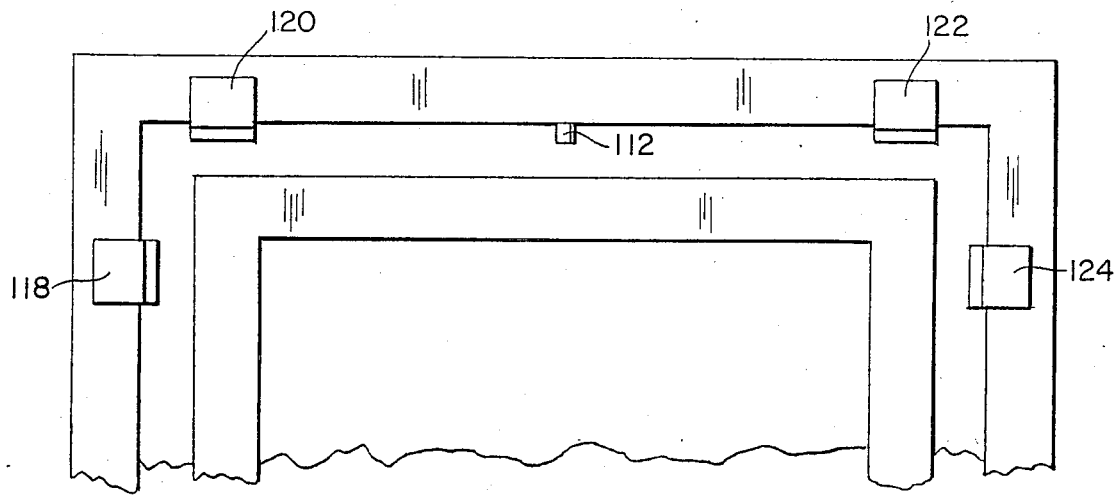
FIG. 3 is a partial inside view of a cover portion of the invention of FIG. 1.

When the cover portion is replaced, guides 118, 120, 122, 124 (FIGS. 2 and 3) help align and center the cover portion on the box portion. As the cover portion is pushed onto the box portion, each pin engages a tapered end portion 126 (FIG. 2) of each respective latch 90, 92 to pivot the latch to its open position. This allows each holding pin 110, 112 to slide along the edge of its respective latch until it is received into its retaining slot and the torsion spring snaps the latch closed.

It will be noted that the conduits will prevent the escape of displaced fuel from their respective associated enclosure in all positions of the heater.

It will also be noted that if there were no outer enclosure 14, and if there were no inner enclosure air holes adjacent inner cap 28 wherein that cap were to function simply as a fluid tight cover, then heater 1 would still be operable. The single conduit 34 would provide the fuel entrapping means, and the ventilation passage 25 associated with cap 26 would sustain combustion of the fuel.

Second Embodiment

A second embodiment of the safety heater is shown in FIG. 4 through 7 and is referred to generally by reference numeral 2. Safety features similar to those of heater 1 are included to prevent fuel leaks and burns, and thereby eliminate fire hazards. This embodiment, however, due to its cylindrical shape and simpler mechanisms is somewhat less expensive to construct than the rectangular safety heater 1.

The safety heater 2 (FIG. 4) comprises a vessel including an inner cylinder, or inner container, 122 which forms a combustion chamber 126 and contains a fuel supply 124. Inner cylinder 122 is capped at both ends by inner caps 128, 130 and is surrounded by an outer cylinder, or outer container, 132 which is capped by outer caps 134, 136.

The inner cylinder is an open-ended tube that has a plurality of evenly spaced tines 138, 140, 142, 144, 146 extending upwardly and inwardly at its upper end. The tines provide a mounting surface for the top inner cap 130. The cap is permanently attached to the tines by welding or fasteners.

The top inner cap 130 has an annular mouth 154 larger than the outer diameter of the inner cylinder 122. A peripheral portion of the cap 130 surrounds an upper end portion of the inner cylinder and is formed into a continuous open conduit 150. The conduit 150 extends below the tine base 152 and thereby prevents the escape of loosened fuel or debris from the combustion chamber 126 if the heater is upset. An air gap between the tine base 152 and the cap 130 (between the inner cylinder 122 and conduit 150) permits gaseous communication between the interior and the exterior of the combustion chamber.

A lower end portion of the inner cylinder 122 extends coaxially into the lower inner cap 128 and surrounds the fuel can 124. The inner cylinder is suspended coaxially above the lower cap 128 by spacer brackets 156, 158, 160, 162 which are permanently affixed to, and between, the inner and outer cylinders (122 and 132). The inner cylinder's lower end 164 is positioned above the inner surface of lower cap 128. Cap 128 is similar to cap 130 and has an annular mouth larger than the outer diameter of the inner cylinder. A peripheral portion of the cap 128 forms a continuous open conduit 165 which surrounds the lower end portion of the inner cylinder. This conduit is positioned adjacent an air gap between the cylinder end 164 and the cap body 128 and thereby prevents the escape of displaced fuel or debris if the heater is upset. An air gap 166, between the conduit 165 and the inner cylinder 122, permits gaseous communication between the interior and the exterior of the combustion chamber.

Centrally fixed within the lower inner cap 128 is a fuel can holder 159 (FIGS. 4 and 5) which comprises two U-shaped brackets 168, 170 fixedly joined to each other at the center of the lower inner cap 128 by a rivet 172. The bracket arms 174, 176, 178, 180 (FIG. 5) are arranged to properly support the fuel can 124. In addition, the upper bracket 170 is slightly arched to compensate for the thickness of bracket 168 at the rivet 172 so that the four bracket arms 174, 176, 178, 180 are all of equal height.

Extending outward from arms 174, 176 are two anchor plates 182, 184 on which are mounted pivot pins 186, 188 and latches 190, 192. Coiled around each of the pivot pins 186, 188 is a respective torsion spring 194, 196, each having an end held in a grooved portion of a respective adjacent spring holder 198, 200. The opposite end of each spring 194, 196 is trapped by a respective bar 202, 204 extending from its associated anchor plate 182, 184 (FIG. 5). Each spring 194, 196 urges its associated latch 190, 192 to a closed position wherein latch heads 206, 208 capture the fuel can 124 in the fuel can holder. When the inner and outer cylinders are removed for access, as discussed hereinafter, finger pressure on the latch heads 206, 208 is sufficient to pivot the latches 190, 192 so that the fuel can 124 can be removed. Angled surfaces 209, 210 lever the latches out of the way when a replacement can is inserted. When a can is seated in the holder 159 below head portions 206, 208, the torsion springs snap the latches shut.

An alternate configuration of the fuel can holder 159 is shown in FIG. 6. This simplified holder 212 operates basically the same way as holder 159 (described hereinbefore) but is less expensive to produce. Two U-shaped brackets 214, 216 are attached to each other and to the lower inner cap 128 (not shown) by a fastener 218. The brackets are coaxial and perpendicular to each other. In this embodiment the primary difference is that the latches 220, 222 are simplified and are constructed of spring metal fastened by rivets 224, 226 to bracket 216. Each latch has a lip 228, 230 in a respective upper portion which serves to trap the fuel can in the holder 212. Operation is exactly as described with reference to the previous embodiment (i.e., finger pressure is used to separate the latches and remove the can). Replacement cans are guided by angled latch surfaces 232, 234 to their seat in the holder.

Figure 4:
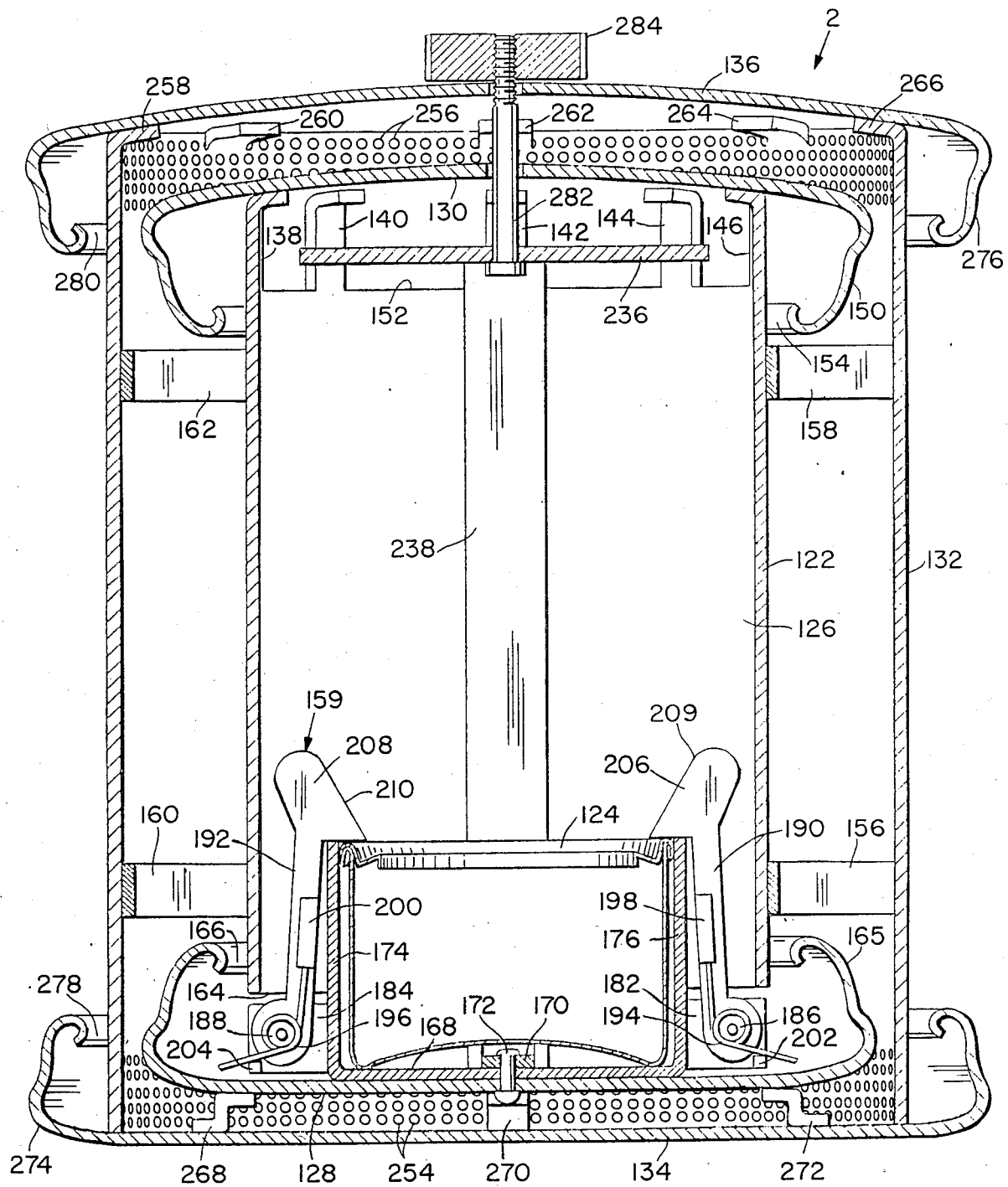
FIG. 4 is a cross-sectional view of a second embodiment of the invention taken along its longitudinal centerline.

Returning now to the primary embodiment of the heater 2, there is positioned adjacent to the combustion chamber 126 and opposite the open end of the fuel can 124 a baffle plate 236 (FIGS. 4 and 7). The baffle plate serves to reflect and evenly spread heat energy from the combustion chamber 126. The baffle plate 236 is held in position, spaced below the upper inner cap 130, by two support bars 238, 240 (FIG. 5). The support bars, each have an upper end attached to the periphery of the baffle plate 236. The support bars 238, 240 extend downward through the combustion chamber and into the lower cap 128. At their lower ends, the support bars have bent portions 246, 248 (FIG. 5) which are fastened with screws 250, 252 or other suitable means to the inside of lower cap 128.

The outer enclosure (comprising outer cylinder 132 and outer caps 134, 136) is somewhat similar to the inner enclosure (comprising inner cylinder 122 and inner caps 128, 130). Several rows of air holes 254, 256 are positioned near the bottom and top of the outer cylinder to promote airflow into and out of the safety heater.

At the top of the outer cylinder a plurality of evenly spaced tabs 258, 260, 262, 264, 266 (others not shown) are bent inwardly to form mounting surfaces for the upper cap 136 which is permanently attached to the tabs by spot welding or suitable fasteners.

The lower end of the outer cylinder merely rests on the inner surface of the lower outer cap 134. The cap 134 is fastened to the lower inner cap 128 by means of equally spaced brackets 268, 270, 272.

Both outer caps 134, 136 are similar in form and function to the inner caps 128, 130 described hereinbefore. However, they are of larger diameter to accommodate the larger diameter of outer cylinder 132. Each outer cap has a peripheral portion formed into a continuous open conduit 274, 276 that surrounds a respective end portion of the outer cylinder. Specifically, the conduits are of sufficient axial length (relative to the cylinder) to conceal the rows of air holes 254, 256 from direct access to the outside environment. Air passages 278, 280 permit gaseous communication, through the air holes, between the interior and the exterior of the cylinders 122, 132. The resulting airflow is sufficient to support efficient combustion of fuel within the heater. Thus, the outer conduits act as redundant safety devices which, while permitting airflow, bar the escape of fuel or debris into the local environment where they might be hazardous.

The safety heater 2 also comprises two permanent subassemblies. A lower subassembly comprises both lower caps 128, 134, the fuel can holder 159 and the baffle plate 236 including the supports 238, 240. An upper subassembly comprises both cylinders 122, 132 and both upper caps 130, 136. The two subassemblies are secured to each other by means of a threaded post 282 which is affixed to the baffle plate 236 (lower subassembly). The post extends through both upper caps 130, 136 to the exterior of the heater. An internally threaded thumbnut 284 is mated with the post to hold the two subassemblies together during use of the heater.

The heater can, therefore, be easily disassembled for access to the combustion chamber by removal of the thumbnut. Access to the combustion chamber is required for lighting and extinguishing the heater as well as for replacing the fuel can 124.

In order to ease reassembly of the heater, four guide tabs 286, 288, 290, 292 (FIG. 5) are positioned at an inner edge of the lower outer cap 134. The tabs help align and position the subassemblies during reassembly of the safety heater.

Third Embodiment

A third embodiment of the safety heater having similar fuel entrapping means as the hereinbefore described embodiments, but having added special features is described hereinafter.

A safety heater 3 (FIG. 8) comprises a vessel including an inner cylinder, or inner container, 304 which forms a combustion chamber 305. Inner cylinder 304 is capped at both ends by inner caps 303, 307 and is surrounded by an outer cylinder, or outer container, 306. Outer cylinder 306 is capped by outer caps 308, 309. A central portion of the lower inner cap 307 is formed into a cup-shaped well or holder 310 which receives a closely fitted fuel can 312. The fuel can contains jelled fuel of the type commonly used for heating portable stoves and chafing dishes. Holder 310 extends downwardly away from the combustion chamber 305.

The inner cylinder is an open-ended tube that has a plurality of evenly spaced tines 313, 314, 316 (a similar fourth tine is sectioned away and is therefore not shown) extending upwardly and inwardly at its upper end. The tines provide a mounting surface for the top inner cap 303. The cap is permanently attached to the tines by welding or fasteners.

The top inner cap 303 has an annular mouth 318 larger than the outer diameter of the inner cylinder 304. A peripheral portion of the cap 303 is formed into a continuous open conduit 320 that surrounds an upper end portion of the inner cylinder. The conduit opening is positioned around the upper end 322 of the inner cylinder. Thus, conduit 320 entraps loosened fuel or debris from the combustion chamber 305 or the fuel can 312 if the heater is upset. An air passage, between the inner cylinder 304 and conduit 320, permits the passage of gases between the interior and the exterior of the combustion chamber.

Top inner cap 303 is permanently attached to top outer cap 308 by means of a mounting ring 324 having a U-shaped cross-section. A leg of the ring's "U" is spot welded or riveted to the inner surface of cap 308. A plurality of evenly spaced L-shaped brackets 326, 327, 328 (a similar fourth bracket is sectioned away and is therefore not shown) each have a leg welded to inner cap 303. An opposite leg of each bracket is welded or riveted to ring 324. Thus, cap 303 is fixed in spaced relation to cap 308 thereby reducing conductive transfer of heat from the former to the latter.

A lower end portion of the inner cylinder 304 extends coaxially into the lower inner cap 307. The inner cylinder's lower end 330 is positioned above the inner surface of lower cap 307. Cap 307 is similar to cap 303 and has an annular mouth 332 larger than the outer diameter of the inner cylinder 304. A peripheral portion of the cap 307 is formed into a continuous open conduit 334 that surrounds the lower end portion of the inner cylinder. The conduit opening surrounds the lower end 330 of the inner cylinder. Thus, conduit 334 entraps loosened fuel or debris from the combustion chamber 305 or the fuel can 312 if the heater is upset. An air passage, between the inner cylinder 304 and conduit 334, permits the passage of gases between the interior and the exterior of the combustion chamber.

In concert, the upper and lower air passages produce an airflow sufficient to support efficient combustion of the fuel in can 312. The conduits are positioned to act as safety devices which, while permitting airflow, bar the escape of fuel or debris into the environment where they might be hazardous.

Extending downwardly from the lower end of the inner cylinder 304 is a plurality of evenly spaced tines 336, 337, 338 (a similar fourth tine is sectioned away and is therefore not shown). Lower end portions of the tines are received in notches (not shown) in the periphery of a circular plate 340 (FIGS. 8 and 9) where the tines are welded to the plate. Plate 340 has a central aperture 342 (FIG. 9) coaxially positioned at the mouth of the fuel can 312. An inner peripheral portion of plate 340, which surrounds aperture 342, is in contact with the top of the fuel can. Thus, gases entering or leaving the interior of the fuel can must pass through aperture 342.

Figure 8:
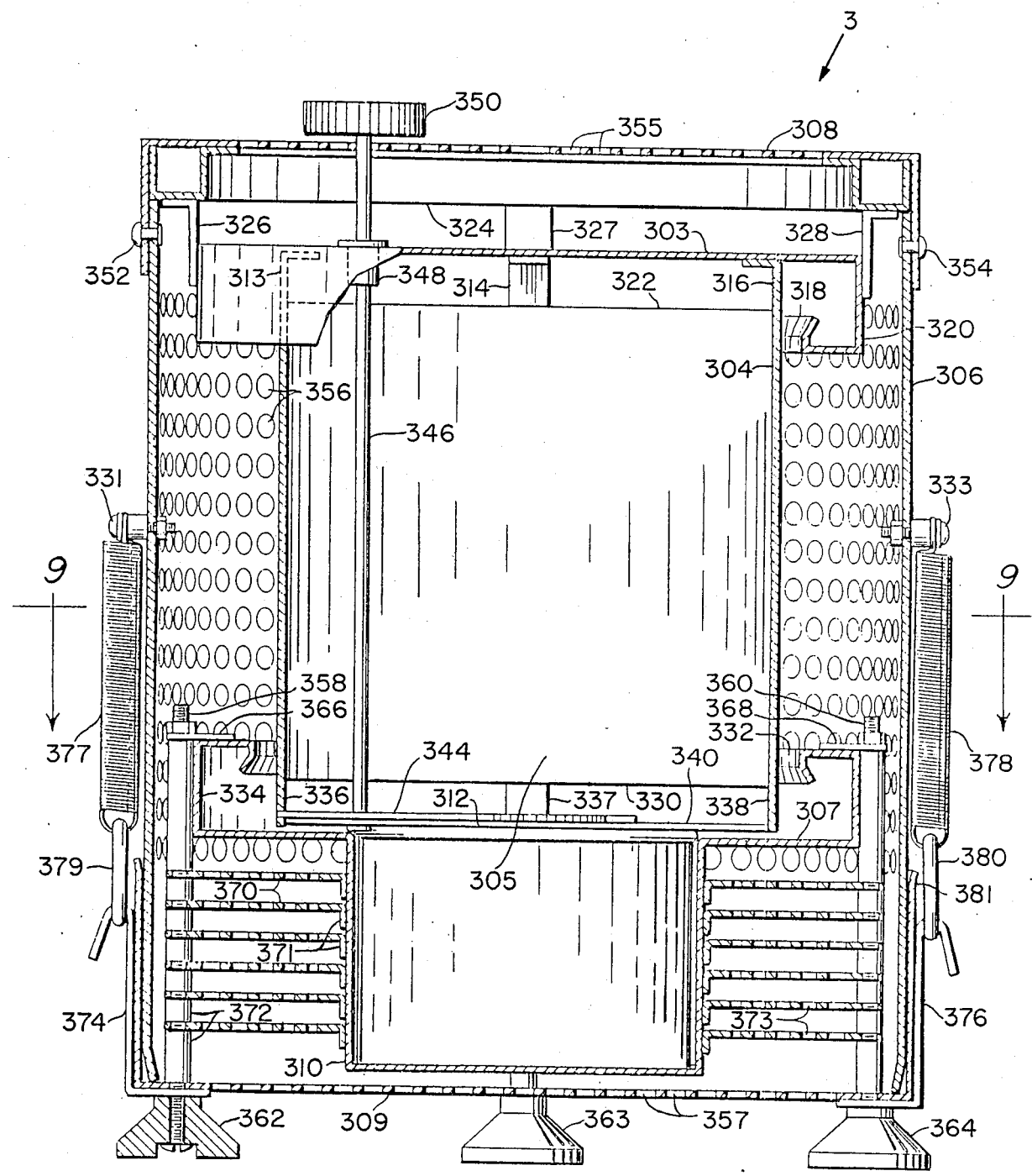
FIG. 8 is a cross-sectional view of a third embodiment the invention taken along its longitudinal centerline.
Figure 9:
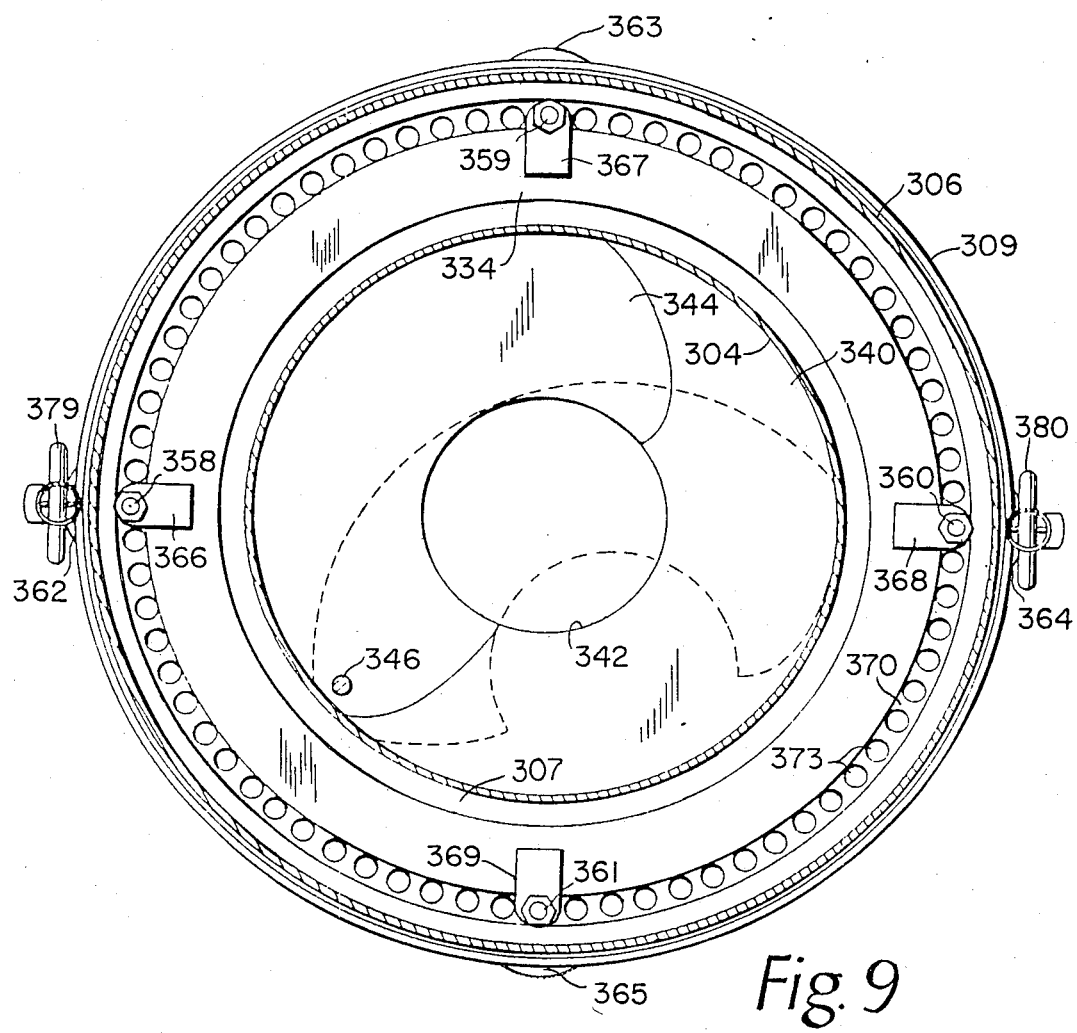
FIG. 9 is cross-sectional view of the invention of FIG. 8 taken along the line 9—9 of FIG. 8.

Pivotally mounted on top of plate 340 is a flame attenuator 344 (FIGS. 8 and 9). The attenuator 344 is fixed to a shaft 346 which has a lower end portion journaled in a small hole drilled through plate 340. The lower end of shaft 346 is flared to prevent the shaft from coming out of the hole. Attenuator 344 can be pivoted, by means of the shaft, between open and closed positions. The attenuator is shaped such that in the open position (shown in FIG. 9) a maximum amount of gases can pass through aperture 342. In the closed position (dashed line in FIG. 9) the attenuator blocks most of aperture 342 to minimize gaseous passage.

An upper portion of the shaft 346 is journaled in a bearing 348 welded to cap 303. The bearing 348 and shaft 346 pass through an aperture in cap 303 so that an upper end portion of the shaft can further extend through an aperture in outer cap 308. A knob 350, fixedly attached to the top end of the shaft, provides a means to pivot the shaft and the flame attenuator. Thus, knob 350 can be used to selectively control the heat output of the safety heater.

Outer cylinder 306, which is coaxial with the inner cylinder 304, is permanently capped at its upper end by cap 308. Rivets 352, 354 hold the cap 308 and cylinder 306 together. Both outer caps 308, 309 and outer cylinder 306 are perforated with perforations 355, 356, 357. Cylinder 306 can be formed from perforated flat stock, such as flattened expanded metal, which can be rolled and the seam can be butt welded. A lower end portion of cylinder 306 is received within the lower outer cap 309 and merely rests on the bottom inner surface of the same.

Lower inner cap 307 is permanently attached, in spaced relation, to lower outer cap 309 by bolts 358, 359, 360, 361 (FIGS. 8 and 9). Sleeve spacers 372, which encircle each bolt, space the caps 307, 309 apart. Each bolt passes through a respective support leg 362, 363, 364, 365, cap 309, and its respective spacers 372. Anchoring each bolt to cap 307 is achieved by passing it through a respective lug 366, 367, 368, 369 welded to the cap.

Encircling the fuel can holder 310 are annular cooling fins 370 having collars 371 (FIG. 8) tightly surrounding the holder. The bolts 358, 359, 360, 361 pass through apertures in peripheral portions of the fins wherein the spacers 372 are placed above and below each fin. Thus, the bolts and spacers help support and evenly space the fins. Each fin 370 is pierced with perforations 373.

The purpose of the fins is to draw heat away from the fuel can holder 310 and fuel can 312 to keep the fuel relatively cool. This helps to keep the fuel burning at an even rate by preventing it from vaporizing excessively at the higher heat settings of the attenuator. Warm air rising from the heater draws relatively cool air through perforations 357 and through the perforations 373 of each fin for heat exchange.

An optional modification (not shown) of the fins 370 includes the elimination of perforations 373. Each fin would then have a plurality of equidistant radial cuts extending inwardly from its outer edge to, but not into, its collar 371. This would divide the fin into a set of blades resembling fan blades. Each blade would also be twisted ninety degrees about its radial axis so that the faces of the blade are substantially vertical. Thus, the fins would resemble impellers wherein air rising between the blades would result in heat exchange.

Figure 10:
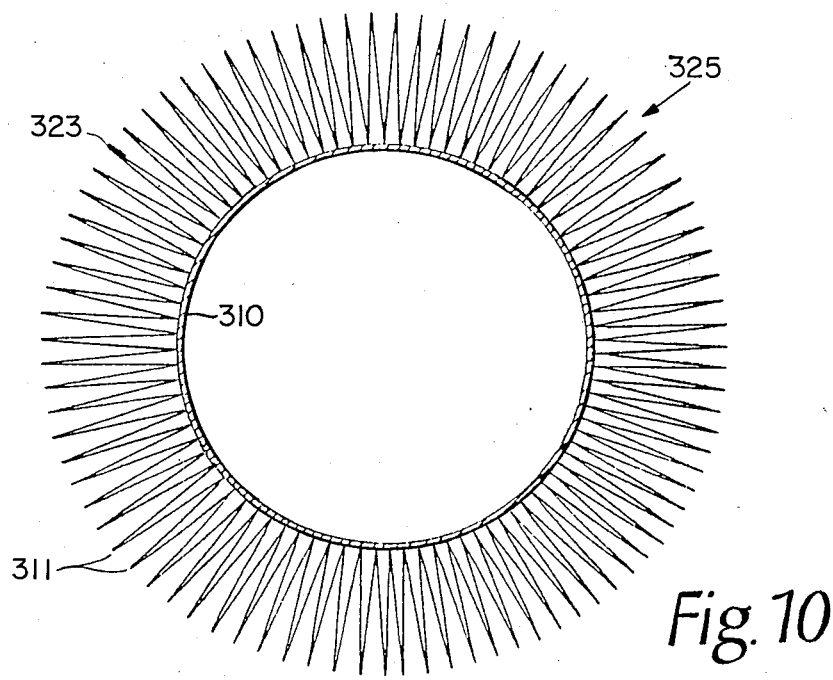
FIG. 10 is a cross-sectional view of a fuel holder of the invention of FIG. 8 taken perpendicularly across its vertical axis and shows a cooling collar encircling the holder.

A simple alternative method of devising cooling fins for fuel holder 310 is shown in FIG. 10. The holder is shown in cross-section surrounded by a cooling collar 325. The collar comprises a plurality of cooling fins 311 which are formed from a single strip of thin metal bent at acute angles in alternating directions. Thus, the largest surfaces of the fins 311 are positioned parallel to the axis of the holder. The two ends of the strip are folded together to form a joint 323. An annular clamp or strap (not shown) can be tightened around the collar 325 to insure firm contact of all the fins with fuel holder 310. A space (not shown) would be left between cap 307 and the top of collar 325 so that air rising between the fins 311 is not trapped under the cap. The vertical height of the fins 311 is substantially equal to the height of holder 310 minus the height of the space mentioned in the previous sentence.

The cooling fins, whichever are used in the invention, are protected from damage by being permanently enclosed between the lower caps 307, 309.

Safety heater 3 also comprises upper and lower permanent subassemblies. The lower subassembly comprises both lower caps 307, 309, fins 370, legs 362, 363, 364, 365, and their associated fastening means. The upper subassembly comprises both cylinders 304, 306, both upper caps 303, 308, plate 340, flame attenuator 344, shaft 346, knob 350, and their associated fastening means. Spring latches secure the two subassemblies together. The latches comprise two hooks 374, 376 (FIG. 8) affixed to diametrically opposite locations on lower cap 309 by bolts 358, 360. End portions of two springs 377, 378 are fixed to diametrically opposite locations on the outer cylinder with fasteners 331, 333. An opposite end portion of each spring 377, 378 is attached to a respective ring 379, 380. Thus, the rings can be placed on the hooks under spring tension to secure the subassemblies together. This latch is simple, yet very effective in preventing accidental separation of the subassemblies. The springs may be chosen with sufficient strength to prevent a child from unlatching the heater.

The heater can be disassembled for access to its interior by unhooking the rings 379, 380. Access to the interior of the heater is required for lighting the fuel and replacement of the fuel can 312.

To guide and facilitate its entry into cap 309, the outer cylinder's lower end portion is curved slightly inward while the top edge the rim 381 of cap 309 is curved slightly outward.

Heat output from the heater can be reduced with the control knob 350 to a level such that the outer cylinder and outer caps can serve as a guard to protect the user from burns. In that operational mode, the user can safely come in close contact with the heater. For example, he can place the device between his feet or on his lap while in a sitting position when watching spectator sports; as in a football stadium. Outdoors, in that position, a blanket or poncho partially covering himself and the heater would trap warm air for greater comfort (proper ventilation considered). If the heater were to be used exclusively for this purpose, it can be modified to keep the heat level permanently low by restricting the flame attenuator selections.

Permanent attachment of components, referred to above as being "welded", may alternatively be fixed with fasteners such as rivets. Note that except for the lugs, all the components of the lower subassembly are held together by only four bolts. This, of course, saves assembly time and expense for production of the heater.

If preferred, the fuel in can 16 of heater 1 (FIG. 1) may be cooled during operation by means of a modification employing the cooling principles used in heater 3. For example, the overall size of heater 1 relative to the can 16 could be larger and short side 18 could have a cup-shaped well to contain the fuel can. Cooling fins could encircle the well.

Each of the described heater embodiments is designed to entrap liquid, solid, or semisolid debris within its continuous conduits if the device is dropped or otherwise upset while operating. The debris are then quickly consumed without hazard. For example, if the heater is tipped over, any displaced fuel simply drips into the cap conduits and is trapped. If the safety heater is placed completely upside-down, the displaced fuel will also be safely entrapped in the conduits. The entrapment system functions in all positions of the heater.

It is understood that various modifications can be made of the embodiments illustrated and described herein without departing from the spirit of the invention as expressed in the following claims.

What is claimed is:

1. A portable safety heater comprising:
   a container having at least one wall and two open ends;
   a fuel source;
   at least two end caps substantially enclosing the open ends of the container wherein the combination encloses the fuel source, the end caps having entrapment means which operate in all positions of the heater for entrapping fuel displaced from the fuel source wherein the combination includes air passages for allowing airflow past the entrapment means to support combustion of fuel therein.

2. The portable safety heater according to claim 1, wherein the entrapment means comprises continuous conduits formed in the end caps to collect fuel displaced from the fuel source as the fuel reaches the vicinity of the air passages.

3. The portable safety heater according to claim 1, further comprising an outer enclosure surrounding the container and the end caps in spaced relation thereto, the outer enclosure having air openings.

4. A portable safety heater comprising:
   A vessel having air passages for allowing airflow through the vessel;

a fuel source retaining fuel for combustion within the vessel wherein the airflow supports the combustion; and means for entrapping fuel which operates in all positions of the heater for preventing fuel from escaping from the vessel through the air passages if the vessel is disturbed, while allowing gases to pass into and out of the vessel.

5. The portable safety heater according to claim 4, further comprising access means for providing access to the interior of the heater in order to permit maintenance of the heater and replacement of fuel therein.

6. A portable safety heater as claimed in claim 4 comprising:

a plurality of cooling fins surrounding the fuel source for dissipating heat from the source into local atmospheric air.

7. The portable safety heater according to claim 6, wherein the cooling fins comprise a plurality of perforated plates positioned adjacent one another in spaced relation, each plate encircling the source.

8. The portable safety heater according to claim 6, wherein the cooling fins comprise a plurality of plates having surfaces positioned substantially parallel to the axis of the source.

9. The portable safety heater according to claim 8, wherein the fins are formed from a single strip of metal bent at acute angles in alternating directions.

10. The portable safety heater according to claim 7, wherein the vessel comprises:

two subassemblies, one detachable from the other and further comprising;

a pair of hooks attached to one of the subassemblies;

a pair of springs, each having an end attached to the other subassembly; and a pair of rings, each attached to an opposite end of each spring, respectively, each ring positioned to detachably link with each hook, respectively, under spring tension for detachably latching the two subassemblies together.

11. The portable safety heater according to claim 4, further comprising:

a plate having an aperture positioned above the fuel source; and a flame attenuator pivotally mounted adjacent the plate and movable between open and closed positions, the attenuator being shaped such that in the open position a maximum amount of gases pass through the plate aperture and in the closed position the attenuator blocks most of the aperture to minimize gaseous passage therethrough.

12. The portable safety heater according to claim 11, further comprising a shaft fixedly attached to the attenuator and an end portion of the shaft extending exteriorly of the heater such that the attenuator can be moved between the open and closed positions by movement of the shaft from the exterior of the heater.

13. A portable safety heater comprising:
a fuel source;
an enclosure for enclosing said fuel source, the enclosure having air passage means for allowing airflow through the enclosure in order to support combustion of fuel from the fuel source; and
at least one conduit, associated with the air passage means, for entrapping fuel displaced from the fuel source thereby preventing the escape of fuel from the heater in all positions of the same.

14. The portable safety heater according to claim 13, further comprising the first mentioned enclosure surrounded and shielded by an outer enclosure.

15. The portable safety heater according to claim 13, further comprising baffle means located within the enclosure to deflect hot gases rising from the combustion chamber.

16. A portable safety heater comprising:
a fuel source;
an enclosure for enclosing said fuel source, the enclosure including a plurality of open conduits, each conduit having a portion in spaced relation to an enclosure wall such that a gap therebetween provides a passage which leads to the interior of the enclosure for gaseous exchange between the interior and exterior of the enclosure for supporting combustion of fuel, wherein the conduits entrap fuel displaced from the fuel source thereby preventing the escape of fuel from the heater in all positions of the same.

17. The portable safety heater according to claim 16, further comprising the first mentioned enclosure surrounded by an outer enclosure, the outer enclosure having a plurality of openings for gaseous passage into and out of the outer enclosure to ventilate the first enclosure, wherein the outer enclosure functions as a protective shield.

18. The portable safety heater according to claim 17, wherein the outer enclosure includes a detachable outer cap and the first enclosure includes a detachable inner cap wherein the inner and outer caps are fixed to each other and detachable as a unit for access to the interior of the heater for fuel replacement and maintenance.

19. The portable safety heater according to claim 18, further comprising at least one latch attached to the heater for locking the caps to the main body of the heater.

20. A portable safety heater comprising:
a fuel source;
an enclosure for enclosing said fuel source, the enclosure having a plurality of conduits, each conduit having a portion contiguous with an enclosure wall for guiding fuel spilled from the fuel source into the conduit to become entrapped therein, the combination of conduits entrapping displaced fuel so that fuel is prevented from escaping from the heater in all positions of the same; and
means for allowing the passage of gases between the interior and the exterior of the enclosure past the conduits for supporting combustion of fuel.

21. The portable safety heater according to claim 20, wherein the fuel source is a can containing a semi-solid fuel.

22. A portable safety heater comprising:
a fuel source;
a double-wall vessel for enclosing said fuel source, the vessel having a plurality of ventilation openings through both vessel walls for allowing free gaseous exchange between the interior and exterior of the vessel to support combustion of fuel; and
a plurality of open conduits, at least a portion of at least one of the conduits positioned outwardly of each respective ventilation opening of at least one vessel wall such that the conduits entrap displaced fuel from the fuel source so that fuel is prevented from escaping from the heater in all positions of the same.

23. A portable safety heater comprising:

a fuel source;

A vessel for containing said fuel source, the vessel having air passages for allowing airflow through the vessel in order to support combustion of fuel from the fuel source therein; and means for entrapping fuel which operates in all positions of the heater for preventing fuel from escaping from the vessel through the air passages if the vessel is disturbed, while allowing gases to pass into and out of the vessel.

* * * * *